(12) United States Patent
Schultz et al.

(10) Patent No.: US 8,906,693 B2
(45) Date of Patent: Dec. 9, 2014

(54) MATERIALS AND METHODS FOR MEASURING NITRIC OXIDE LEVELS IN BIOLOGICAL FLUIDS

(75) Inventors: Gregory S. Schultz, Gainesville, FL (US); Daniel J. Gibson, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 34 days.

(21) Appl. No.: 13/322,012

(22) PCT Filed: Jun. 3, 2010

(86) PCT No.: PCT/US2010/037257
§ 371 (c)(1),
(2), (4) Date: Jan. 27, 2012

(87) PCT Pub. No.: WO2010/141719
PCT Pub. Date: Dec. 9, 2010

(65) Prior Publication Data
US 2012/0136054 A1    May 31, 2012

Related U.S. Application Data

(60) Provisional application No. 61/183,775, filed on Jun. 3, 2009.

(51) Int. Cl.
*G01N 33/84* (2006.01)
*G01N 33/50* (2006.01)
*G01N 33/58* (2006.01)

(52) U.S. Cl.
CPC .............. *G01N 33/582* (2013.01); *G01N 33/84* (2013.01); *G01N 2800/20* (2013.01)
USPC ...................... 436/116; 422/82.08; 422/82.05

(58) Field of Classification Search
CPC ..... G01N 33/582; G01N 33/84; G01N 33/58; G01N 33/50; G01N 2800/20
USPC .............................. 436/116; 422/82.08, 82.05
See application file for complete search history.

(56) References Cited

U.S. PATENT DOCUMENTS

| 4,631,255 | A | 12/1986 | Takino et al. |
| 8,058,024 | B2 * | 11/2011 | Schultz et al. .................. 435/23 |
| 2004/0190813 | A1 | 9/2004 | Kopelman et al. |
| 2004/0203068 | A1 * | 10/2004 | Mannick et al. ............... 435/7.1 |
| 2008/0166792 | A1 | 7/2008 | Attar et al. |
| 2009/0258382 | A1 * | 10/2009 | Schultz et al. .................. 435/23 |
| 2009/0286225 | A1 * | 11/2009 | Wheeler et al. .................... 435/5 |

FOREIGN PATENT DOCUMENTS

| KR | 10-2004-0090356 | 10/2004 |
| WO | WO 98/20336 | 5/1998 |
| WO | WO 2008/012642 | 1/2008 |

OTHER PUBLICATIONS

Gibson et al., "Chronic wound diagnostic for matrix metalloproteinase", *Wound Healing Southern Africa*, 2009, vol. 2, No. 2, pp. 68-70.
Kojima et al., "Bioimaging of Nitric Oxide with Fluorescent Indicators Based on the Rhodamine Chromophore", *Analytical Chemistry*, 2001, vol. 73, No. 9, pp. 1967-1973.
Schäffer et al., "Nitric Oxide Regulates Wound Healing", *Journal of Surgical Research*, 1996, vol. 63, No. 1, pp. 237-240.
Witte et al., "Role of nitric oxide in wound repair", *The American Journal of Surgery*, 2002, vol. 183, No. 4, pp. 406-412.

* cited by examiner

*Primary Examiner* — Christine T Mui
(74) *Attorney, Agent, or Firm* — Saliwanchik, Lloyd & Eisenschenk

(57) ABSTRACT

The subject invention presides novel devices and methods for the measurement of nitric oxide in biological samples, including wound fluid samples. These advantageous devices and methods can be used for clinicians to monitor the wound's nitric oxide metabolism and/or response to treatment.

20 Claims, 3 Drawing Sheets

MATERIALS AND METHODS FOR MEASURING NITRIC OXIDE LEVELS IN BIOLOGICAL FLUIDS

CROSS-REFERENCE TO A RELATED APPLICATION

This application claims the benefit of U.S. provisional application Ser. No. 61/183,775, filed Jun. 3, 2009, which is incorporated herein by reference in its entirety.

BACKGROUND OF INVENTION

The rapid and accurate detection of target molecules is critical for many areas of research and medical diagnosis. Important features for a diagnostic technique to be used for the detection of analytes are specificity, speed, and sensitivity. Time constraints and ease of on-site analysis can be major limitations.

Since its discovery in 1987 (Palmer, R. M. J. et al., 1987, *Nature*, 327:524-527), nitric oxide (NO) has been implicated in disparate pathologies including: metastasis of cancerous cells (Anbar, M. and Gran, B. M. 1997, *Journal of Pain and Symptom Management*, 14:225-254), inflammation in the airway of an asthmatic (Batra, J. al., 2007, *Thorax*, 62:16-22.), onset of hypercholesterolemia, atherosclerosis, and hypertension diseases (Gibaldi, M. 1993, *J. Clin. Pharmacol.*, 33:488-496; Star, R. A. 1993, *Am. J. Med. Sci.*, 306:348-358; Tanner et al., 1993, *Sem. Thrombosis Hemostasis*, 19:167-175), massive infection and septic shock, and regulation of wound healing.

Generation of nitric oxide by naturally occurring, endogenous, processes has been demonstrated by several studies to correlate with wound healing (Schäffer, M. R. et al., 1996, *Journal of Surgical Research*, 63:237-240; Witte, M. B. and Barbul, A. 2002, *The American Journal of Surgery*, 183:406-412). Briefly, wound collagen accumulation can be stimulated by arginine and, during wound healing, nitric oxide is produced from oxidation of L-arginine by a family of enzymes known as nitric oxide synthases. Conversely, low levels of nitric oxide generation indicate a delayed or inhibited healing response, which is often associated with chronic, non-healing wounds.

Unfortunately, direct measurement of nitric oxide is difficult due to its half-life in vivo of only a few seconds or less. Therefore, stable nitric oxide metabolites, nitrite ($NO_2^-$) and nitrate ($NO_3^-$), are widely used as surrogates for indirect determination of nitric oxide in biological fluids. Nitric oxide metabolites are currently measured using time and labor intensive techniques (e.g., the Griess reaction) that also require expensive equipment (e.g., spectrophotometer, fluorometer, and/or plate reader). Thus, rapid, point-of-care diagnostic methods and devices for nitric oxide are needed.

BRIEF SUMMARY

The present invention provides diagnostic methods and devices that can be used to assay a medium, such as tissue in vivo or a sample in vitro, in order to determine the presence and/or quantity of nitric oxide.

The ability to detect nitric oxide according to the subject invention is useful in order to direct therapy and/or prophylaxis. Thus, the devices and methods of the invention can be of great benefit when diagnosing (and implementing a treatment for) a pathological condition that can be evaluated through the presence or absence of nitric oxide.

In an embodiment that is specifically exemplified herein, the subject invention provides assays that can be used to determine and/or monitor the status of a wound, thereby facilitating the administration of appropriate care and treatment. In a specific embodiment, the assays of the subject invention can be used to improve treatment of a chronic wound.

For example, a non-healing (chronic) wound is associated with low levels of nitric oxide metabolites, including nitrite $NO_2^-$). Thus, nitrite is one target analyte for the assays of the present invention.

Assay formats that can be used in accordance with the subject invention include, but are not limited to, fluorometric and colorimetric assays.

In a specific embodiment exemplified herein, the subject invention provides a rapid and accurate assay for qualitatively and/or quantitatively assessing nitric oxide metabolites in a sample taken from a wound. Specifically exemplified herein is a fluorometric or colorimetric assay that, through an indicator molecule that reacts with nitrite under oxidizing and acidic conditions, provides a detectable change in fluorescence (increase, decrease, or fluorescent color) or visible absorbance hue/color. The use of this assay makes it possible to quickly and accurately assess the quantity of nitric oxide metabolites in a sample taken from a wound.

Advantageously, in certain embodiments, the subject invention provides assays that can be self-contained in a single unit. This facilitates conducting assays in the field and, in the case of healthcare, at the point of care.

The assays are quick and easy-to-use. In specific embodiments, the assay can be carried out by, for example, a nurse utilizing either no instrumentation or only minimal instrumentation. In one embodiment, information about the status of a wound can be readily, easily and reliably generated in 10 minutes or less. Information about the wound can include, but is not limited to, nitric oxide presence and/or quantity.

Upon conducting the simple procedures of the subject invention, a physician has very important information to treat a condition in an as-needed manner. This information can also be used to design and justify subsequent and related treatments as required by the majority of insurance companies. The assays of the subject invention can also be used prior to the application of pharmaceutical agents and/or grafts to ensure that the recipient site is conducive to the therapy (e.g. any tissue or protein applied to the site will not be adversely affected by the presence of nitric oxide).

DETAILED DISCLOSURE

Figure 1:
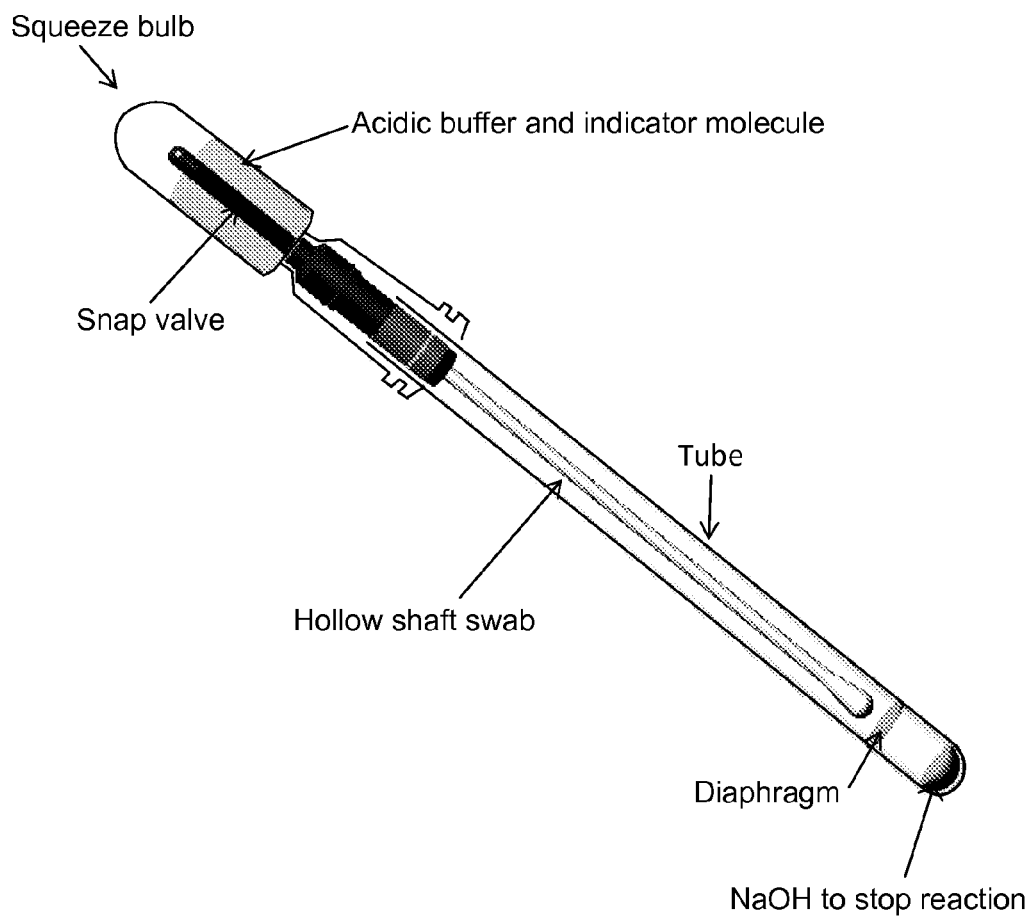
FIG. 1 is a device useful according to the subject invention.

The present invention provides diagnostic methods and devices for measuring nitric oxide in a sample. The sample may be, for example, an in vivo tissue sample or an in vitro sample (e.g, biological sample or environmental sample).

The assays of the subject invention can be used as part of a program to optimize (or at least improve) treating and/or routing in a hospital. In a preferred embodiment, the assays of the subject invention are used to measure the level of nitric oxide present in a wound.

Advantageously, in certain embodiments, the subject invention provides assays that can be self-contained in a single unit. This facilitates conducting assays in the field and, in the case of healthcare, at the point of care.

In an embodiment that is specifically exemplified herein, the subject invention provides assays that can be used to determine and/or monitor the status of a wound. The assays are quick and easy-to-use. In specific embodiments, the assay can be carried out by, for example, a nurse utilizing either no instrumentation or only minimal instrumentation. In one embodiment, information about the status of a wound can be readily, easily and reliably generated in 30 minutes or less. In a preferred embodiment, the results are obtained in 15 minutes or less. Most preferably, the results are generated in 10 minutes or less. Information about the wound can include, but is not limited to, quantity of nitric oxide metabolites. The assays may also measure other biochemical markers associated with the status of a wound and/or the healing process.

In a specific embodiment, the assay of the subject invention is utilized to assess the status of chronic wounds by determining the presence and/or quantity of nitric oxide metabolites. As used herein, reference to "chronic wounds" refers to wounds that after 2 weeks are not healing properly.

The assay of the subject invention is particularly advantageous because, through the careful selection of various parameters, including the indicator molecules, the assay exhibits rapid kinetics with excellent accuracy and minimal background interference. The devices and methods of the invention can be of great benefit when diagnosing a pathological condition that has one or more biochemical markers. For example, a non-healing (chronic) wound is marked by a low level of nitric oxide.

In a preferred embodiment, the subject invention utilizes a $NO_2^-$ detection assay. A variety of assay formats can be used according to the subject invention. Particularly preferred assays as described herein include fluorometric and colorimetric assays.

The subject invention also provides sample collection methodologies which, when combined with the assays of the subject invention, provide a highly advantageous system for analyte evaluation in a wide variety of settings. In one embodiment, a "swab-in-a-straw" collection and assay system can be utilized as described herein.

Simple "mix-and-read" assays minimize time and increase productivity; assays can be for naked eye or quantitative assessment using well-established, relatively inexpensive detection technologies. Advantageously, less equipment and fewer lab skills are necessary to conduct the assays.

Due to the ability to easily, quickly and accurately determine the presence and/or quantity of the target analytes, the devices and methods of the invention facilitate medical diagnoses at a physician's office and/or at the bedside of the patient. Analysis of bodily fluid samples using a device or method of the present invention facilitates timely interventions for time-sensitive conditions or diseases.

The devices and methods of the invention can be used for dermal applications, e.g., to assess the presence of analytes in tissue or wound fluids that are of diagnostic value in assessing wound healing. The molecule(s) targeted for detection and/or measurement can be, for example, nitric oxide.

The devices and methods of the invention can also be used for pulmonary applications, e.g., to assess the presence of inflammation in the airway that are of diagnostic value in assessing asthma. Again, the molecule(s) targeted for detection and/or measurement can be for example, nitric oxide.

The assays of the subject invention can be used to measure the nitric oxide metabolite levels in wound fluids, which is an indicator of anticipated healing or chronicity. Additionally, prior to attaching a graft or treating with a growth factor the nurse/doctor can ensure that the host environment is amenable to the graft/growth factor (i.e. that the graft/growth factor will not be destroyed).

The devices and methods of the subject invention can also be used for cancer detection applications, e.g., to assess the presence of nitric oxide as a direct indicator of a cancerous lesion.

Optionally, in the various embodiments of the invention, the diagnostic method further comprises comparing the concentration of the target molecule in the medium (e.g., a bodily fluid), as determined above, to pre-existing data characterizing the medium (e.g., concentration of the same target molecule in the same patient or a different patient). The target molecule concentration may be that specific target molecule concentration observed under particular conditions.

Optionally, the method of the invention further comprises monitoring the presence and/or concentration of one or more target molecules in a medium over a period of time.

Assays that can be used according to the subject invention to assay for nitric oxide metabolites include assays based on reaction between nitrite and the indicator molecule, which results in a detectable change in fluorescence or visible absorbance hue/color. These assays may be, for example, fluorometric or colorimetric assays.

In one embodiment, the system can include the capability to chemically reduce nitrate in the sample to nitrite, allowing it to be measured indirectly by assaying for nitrite. This approach increases sensitivity by increasing the amount of detectable species, provides a more accurate reading of nitric oxide production in that it measures both stable end products (nitrite and nitrate) of nitric oxide metabolism, provides a means of discerning the relative ratios of nitrate to nitrite which is indicative of the state of the biological sample taken.

The means of reducing nitrate LU nitrite include small moleeule reducing agents such as hydrazine sulfate in normal or basic conditions(Kamphake et al 1967), metal catalysts such as a cadmium-copper in basic conditions (Wood E D, et al, 1967), or enzymatic reduction using enzymes such as Aspergillis Niger nitrate reductase in the presence of the required cofactor NADPH.

The incorporation of the nitrate reduction step necessitates a means of modulating the pH from the basic pH required for reduction, to the low pH required for the nitrate detection reaction, back to normal pH for spectrophotometric, fluorometric, or visual measurement.

The system is also capable of operating without a step to reduce nitrate to nitrite. The total amount of nitric oxide metabolites in a sample can be deduced from the type of biological sample and the typical ratio of nitrite to nitrate in that sample using an empirically determined algorithm. Wound fluid measurements have demonstrated that nitrate levels are approximately 10-fold higher than nitrite levels, while serum levels of nitrate have been measured as being approximately 100-fold higher than nitrite levels. An example algorithm or wound fluids follows:

$$C_{NO} \sim C_{NO2} + C_{NO2}$$

$$C_{NO2} \sim 10 \times C_{NO2}$$

$$C_{NO} \sim C_{NO2} + 10 \times C_{NO2}$$

$$C_{NO} \sim C_{NO2}(1+10)$$

$$C_{NO} \sim 11 \times C_{NO2}$$

which accounts for the 10 fold higher $NO_3$ and 1× for $NO_2$: (10+1) * $NO_2$.

Figure 2:
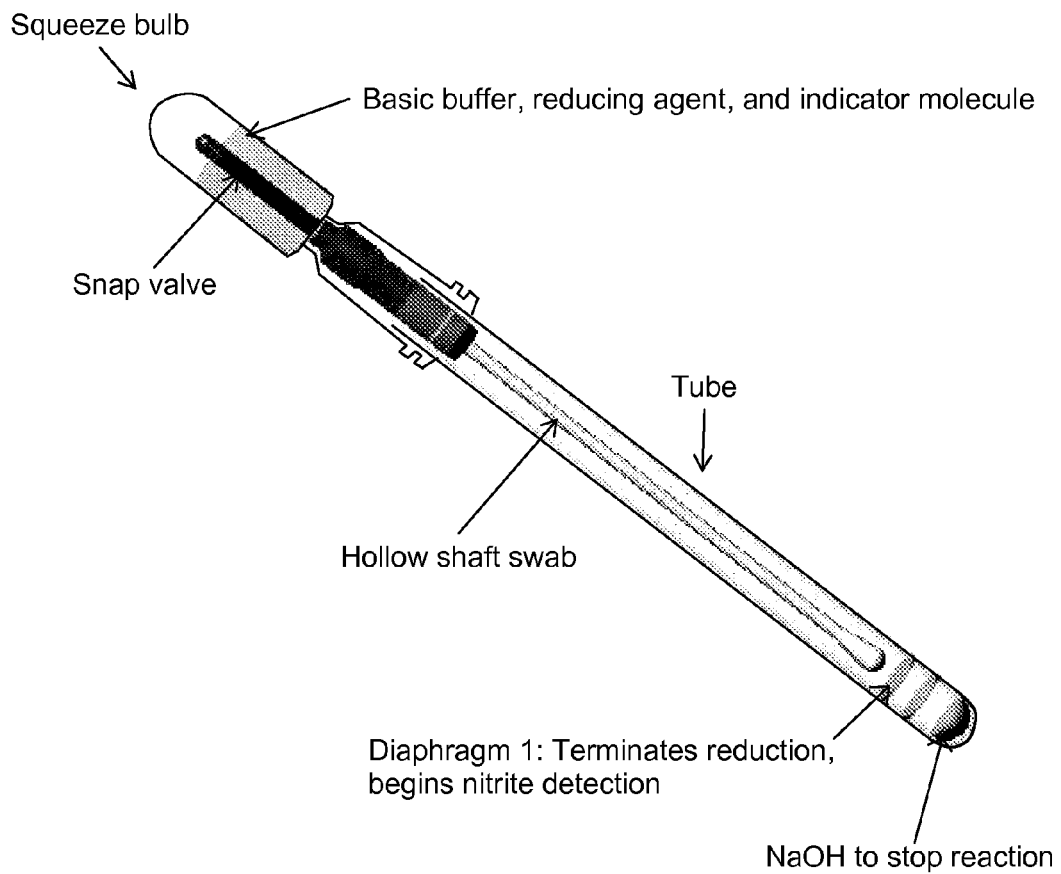
FIG. 2 is a device useful according to the subject invention.
Figure 3:
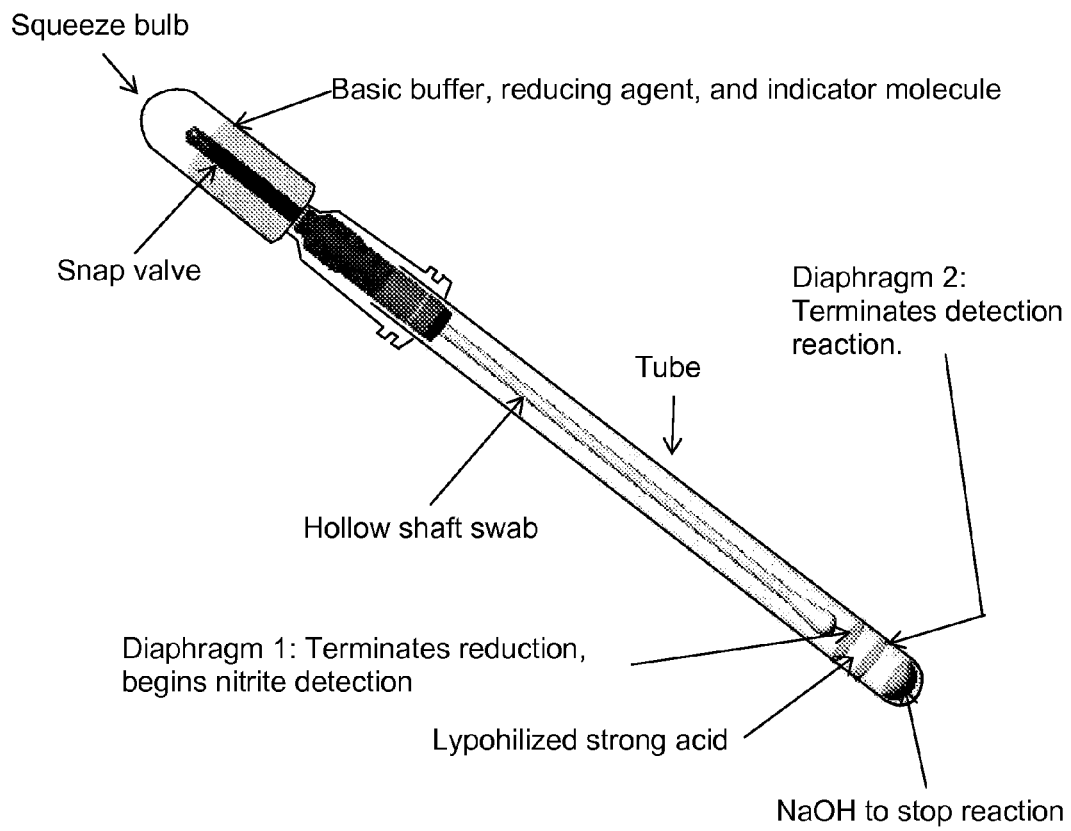
FIG. 3 is a device useful according to the subject invention.

Examples of devices useful according to various embodiments of the subject invention are shown in FIGS. 1, 2, and 3.

The following examples illustrate procedures for practicing the invention. These examples should not be construed as limiting. It will be apparent to those skilled in the art that the examples involve use of materials and reagents that are commercially available from known sources, e.g, chemical supply houses, so no details are given respecting them.

Example 1

Nitrite Detection Assays

The quantity and/or presence of nitric oxide can be determined using $NO_2^-$ detection assays wherein the quantity is determined by the change in fluorescence or color of the indicator molecule after reaction with nitrite under particular conditions.

In one embodiment, the indicator molecule possesses at least one pair of proximal amines and/or a hydrazine group, which, in the presence of nitrite under oxidizing and acidic (low pH) conditions, undergo an acid catalyzed reaction resulting in the formation of a triazole ring. This causes the molecule to undergo a detectable change in fluorescence (increase, decrease, or fluorescent color) or visible absorbance hue/color. Examples of such molecules include diaminofluorescein-based molecules (e.g., DAF-2, DAF-5, DAF-EM), 2,3-diaminonaphthalene (DAN), and NBD hydrazine.

At t=0, the indicator molecule is exposed to the sample in a suitable assay solution that is then mixed to allow the reaction to proceed under oxidizing and acid (low pH) conditions. After a sufficient reaction time, which allows production of a detectable optical change of the assay solution, a stop agent can be added to the mixture to stop this reaction. The stop agent can, for example, adjust the pH of the solution.

The nitrite concentration can then be determined by measuring the change in fluorescence or absorbance color.

In one embodiment, a fluorescence quenching method is used for determining trace amounts of nitrite. According to the subject invention, fluorescent dyes (such as rhodamine dyes including, but not limited to, rhodamine B, rhodamine 6G, rhodamine 110, and rhodamine 123 and rhodamine derivatives including, but not limited to, tetramethylrhodamine (TAMRA), tetramethyl rhodamine isothiocyanate (TRITC), sulforhodamine 101 (and its sulfonyl chloride form Texas Red), Rhodamine Red, and Alexa Fluor dyes such as Alexa 546, Alexa 555, Alexa 633, DyLight 549, and DyLight 633) that react with nitrites to form a product that exhibits less fluorescence can be used. In a preferred embodiment, the nitrite is reacted with rhodamine 110 in an acidic medium to form a new compound, which has much lower fluorescence (i.e., quenched fluorescence or a loss of signal). With a linear range of $1 \times 10^{-8}$ to $3 \times 10^{-7}$ moles/L and a detection limit of $7 \times 10^{-10}$ moles/L, this system (i.e. loss of signal) can be used to directly measure the amount of nitrite and provide a signal that is proportional to the amount of treatment (topical arginine) required. For instance, a patient who has low nitrite levels (or low nitrite nitrate) would have a high fluorescence signal and would require a high dose. Conversely, a patient with high NO metabolites, or with levels considered good/beneficial/sufficient, the system would be calibrated such that no signal (due to quenching) would be generated and therefore no treatment would be needed.

Example 2

Fluorometric or Colorimetric Device

In one embodiment, the subject invention provides methods and devices for rapid and accurate quantitative measurement of nitric oxide metabolites by utilizing a fluorometric or colorimetric assay format.

The fluid sample can be collected using standard clinical methods. In this embodiment, the sample can be collected with a Dacron swab with a hollow shaft that is in communication with a "snap valve" that temporarily separates the swab's hollow center with a reservoir containing a suitable buffer and the indicator molecule as described above at a concentration dictated by the desired assay time frame and desired dynamic range.

The device can also comprise a tube into which the swab can be inserted. The tube possesses at least two chambers, each separated by a penetrable divider, such as a diaphragm. The chamber represents different stages in the chemical reaction being used to measure the nitric oxide metabolites. The first reaction chamber serves to expose the wound fluid to the indicator molecule under oxidizing conditions. After a predetermined amount of time, the swab can be used to penetrate the diaphragm and thereby convey the reaction materials to the second chamber. The second chamber can contain reagents that stop the reaction and/or adjust the pH so that the indicator molecule's signal can be measured.

This device can comprise various components including, for example, (1) a buffer storage chamber, (2) elution buffer, containing an indicator molecule, (3) a snap valve, (4) an elution and reaction chamber, (5) a cap separating the buffer storage chamber and the reaction chamber, (6) a hollow swab-suspension shaft, (7) a sample collection swab, (8) a stop and read chamber containing stop/pH adjusting agent, and (9) a thin penetrable divider separating the elution and reaction chamber and the stop and read chamber.

To determine the concentration of nitrite, the device can further comprise an algorithm that relates the amount of nitrite to the total amount of nitrite and nitrate collectively. In one embodiment, the algorithm consists of multiplying the concentration of nitrite by 10.

This device provides a method of rapid quantification of nitric oxide metabolites in wound tissue. In one embodiment, the incubation time of the reaction is around 10 minutes. Therefore, by using this device, the caregiver is able to quantify the level of nitric oxide in the actual wound in a short time and give necessary treatment immediately.

This assay can be practiced in the following steps, (1) apply the swab to wound debridement and collect wound fluid sample; (2) pull the snap valve to release elution buffer containing the indicator molecule. As elution buffer drains down the straw to perfuse the swab, wound sample is eluded from the swab, making nitrite in wound fluid available to the indicator molecule for reaction; (3) wait for the reaction; (4) push down the swab to perforate the thin penetrable divider, allowing the reaction mixture into the stop and read chamber (the agent adjusts the pH and stops the reaction); and (5) insert the entire device into a fluorometer or spectrometer to read the result.

Example 3

Biological Samples

The devices and methods of the subject invention can be used to detect and/or quantify the presence and/or quantity of nitric oxide in a variety of biological samples. The devices according to the subject can be used to assay various samples as follows:

A. Wound Fluids (Chronic Wounds)
   Obtained by:
   1. Swab
   2 Vac
   3. Bandage/dressing
   4. Capillary/pipette
   5. Syringe
   6. Test run in-vivo in the wound
   7. Tissue biopsy
B. Tear Fluid
   Obtained by:
   1. Wicking paper/material
   2. Capillary/pipette
   3. Syringe
C. Vaginal Fluid
   Obtained by:
   1. Swab
   2. Capillary/pipette
   3. Panty liner
   4. Tampon
   5. Wicking paper/material
   6. Syringe
   7. Tissue biopsy
D. Oral Fluids
   1. Saliva
      Obtained by:
         a. Patient spitting into receptacle
         b. Cheek swab
         c. Capillary/pipette
         d. Wicking paper/material
         e. Syringe
         f. Tissue biopsy
   2. Crevicular fluid (periodontal space)
      Obtained by:
         a. Syringe
         b. Capillary/pipette
         c. Collected scrapings
         d. Wicking paper/material
         e. Swab
         f. Tissue biopsy
E. Nasal
   Obtained by:
   1. Collection of naturally evacuated fluids (runny nose)
   2. Forced evacuation (blowing one's nose) into receptacle
   3. Swab
   4. Flushing
   5. Capillary/pipette
   6. Wicking paper/material
   7. Syringe
   8. Tissue biopsy
F. Throat
   Obtained by:
   1. Forced evacuation (coughing) into/onto receptacle
   2. Swab
   3. Flushing-gargling-spitting
   4. Capillary/pipette
   5. Wicking paper/material
   6. Syringe
   7. Tissue biopsy
G. Otological (Ear)
   Obtained by:
   1. Swab
   2. Flushing
   3. Capillary/pipette
   4. Wicking paper/material
   5. Syringe
   6. Tissue biopsy
H. Axilla
   Obtained by:
   1. Swab
   2. Flushing
   3. Capillary/pipette
   4. Wicking paper/material
   5. Syringe
   6. Clothing (sweat)
   7. Tissue biopsy
I. Pulmonary (Lung)
   Obtained by:
   1. Forced evacuation (coughing) into/onto receptacle
   2. Swab
   3. Capillary/pipette
   4. Wicking paper/material
   5. Syringe
   6. Vac
   7. Tissue biopsy
J. Cyst
   Obtained by:
   1. Swab
   2. Capillary/pipette
   3. Wicking paper/material
   4. Syringe
   5. Vac
   6. Tissue biopsy
K. Synovial Fluid/Connective Tissue
   Obtained by:
   1. Swab
   2. Capillary/pipette
   3. Wicking paper/material
   4. Syringe
   5. Vac
   6. Tissue biopsy
L. Urological
   Urethra
M. Feces
N. Urine
O. Blood
P. Semen
Q. Vomit All patents, patent applications, provisional applications, and publications referred to or cited herein, supra or infra, are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application.

We claim:

1. A device for determining a presence of and/or a concentration of nitric oxide in a biological sample, comprising:
   an enclosed buffer storage chamber containing an elution buffer with an indicator molecule;
   an elution and reaction chamber operably connected to the enclosed buffer storage chamber;
   a hollow swab-suspension shaft attached to a sample collection swab for collecting a sample;
   a valve disposed within the buffer storage chamber and operably connected to the hollow swab-suspension shaft, whereby activation of the valve causes the elution buffer in the buffer storage chamber to flow through the hollow swab-suspension shaft to elute the sample from the collection swab and contact the sample with the indicator molecule;

a stop and read chamber containing at least one agent that stops the reaction initiated by the indicator molecule and/or adjusts pH; and a penetrable divider separating the elution and reaction chamber from the stop and read chamber, wherein the swab-suspension shaft can penetrate the divider when the buffer storage chamber is advanced towards the penetrable divider, such that, after the divider is penetrated, the eluted sample in the elution buffer advances to the stop and read chamber where it remains for determining the presence and/or concentration of nitric oxide.

2. The device according to claim 1, wherein said indicator molecule possesses at least one pair of proximal amines or a hydrazine group, wherein said molecule in the presence of nitrite ($NO_2^-$) under oxidizing and acidic conditions undergoes a reaction resulting in said molecule undergoing a detectable change in fluorescence or visible absorbance hue/color.

3. The device according to claim 2, wherein said indicator molecule is selected from diaminofluorescein-based molecules, 2,3-diaminonaphthalene (DAN) and NBD hydrazine.

4. The device according to claim 3, wherein said diaminofluorescein-based molecule is DAF-2, DAF-5, or DAF-FM.

5. The device according to claim 2, wherein said indicator molecule is selected from rhodamine B, rhodamine 6G, rhodamine 110, rhodamine 123, tetramethylrhodamine (TAMRA), tetramethyl rhodamine isothiocyanate (TRITC), sulforhodamine 101, sulforhodamine 101 acid chloride (Texas Red), Rhodamine Red, Alexa 546, Alexa 555, Alexa 633, DyLight 549, and DyLight 633.

6. The device, according to claim 4, wherein the buffer storage container comprises a cap that operably connects to the elution and reaction chamber.

7. The device, according to claim 6, wherein determining the presence and/or concentration of nitric oxide comprises inserting the device into a fluorometer or spectrometer to detect the presence and/or concentration of the indicator molecule.

8. A method of determining a presence and/or an amount of nitric oxide in a biological sample, comprising:

utilizing a device, according to claim 1, providing, with the elution buffer in the buffer storage chamber of the device, an indicator molecule that possesses at least one pair of proximal amines or a hydrazine group, wherein said molecule in the presence of nitrite ($NO_2^-$) under oxidizing and acidic conditions undergoes a reaction resulting in a detectable change in fluorescence or visible absorbance hue/color;

inserting the biological sample on the sample collection swab of the device into the elution and reaction chamber;

releasing the buffer and the said molecule into the hollow swab-suspension shaft so that the biological sample is eluted from the sample collection swab and the molecule contacts the sample under oxidizing and acid conditions for a sufficient time in the elution and reaction chamber for the reaction to occur;

advancing the hollow swab-suspension shaft towards the penetrable divider, so as to penetrate the penetrable divider;

stopping the reaction by allowing the reacted biological sample to move into the stop and read chamber through the penetrated penetrable divider;

measuring, based on the fluorescence and/or visible color, the concentration of nitrite in said reacted biological sample; and correlating the nitrite measurement with a presence and/or amount of nitric oxide.

9. The method according to claim 8, wherein said indicator molecule is selected from diaminofluorescein-based molecules, 2,3-diaminonaphthalene (DAN) and NBD hydrazine.

10. The method according to claim 9, wherein said diaminofluorescein-based molecule is DAF-2, DAF-5, or DAF-FM.

11. The method according to claim 8, wherein said indicator molecule is selected from rhodamine dyes and rhodamine derivatives.

12. The method according to claim 11, wherein said indicator molecule is selected from rhodamine B, rhodamine 6G, rhodamine 110, rhodamine 123, tetramethylrhodamine (TAMRA), tetramethyl rhodamine isothiocyanate (TRITC), sulforhodamine 101, sulforhodamine 101 acid chloride (Texas Red), Rhodamine Red, Alexa 546, Alexa 555, Alexa 633, DyLight 549, and DyLight 633.

13. The method according to claim 8, wherein there is more than one indicator molecule.

14. The method according to claim 1, wherein results are obtained in less than 10 minutes.

15. The method according to claim 8, which further comprises adopting a treatment plan based, at least in part, on how much nitric oxide is indicated to be present.

16. The method according to claim 15, wherein a L-arginine supplementation is administered if promoting wound healing is needed.

17. The method according to claim 8, wherein said sample is taken from a wound.

18. The method according to claim 17, wherein said wound is a chronic wound.

19. The method, according to claim 8, wherein nitrate in the sample is converted to nitrite prior to contacting the sample with the indicator molecule.

20. The method, according to claim 8, wherein measuring the concentration of nitric oxide comprises inserting the device into a fluorometer or spectrometer to detect the presence and/or concentration of the indicator molecule.

* * * * *

UNITED STATES PATENT AND TRADEMARK OFFICE
CERTIFICATE OF CORRECTION

PATENT NO.         : 8,906,693 B2
APPLICATION NO.    : 13/322012
DATED              : December 9, 2014
INVENTOR(S)        : Gregory S. Schultz et al.

It is certified that error appears in the above-identified patent and that said Letters Patent is hereby corrected as shown below:

In the Specification

Column 1,
Lines 8-10, "claims the benefit of U.S. provisional application Ser. No. 61/183,775, filed Jun. 3, 2009, which is incorporated herein by reference in its entirety." should read --is a National Stage Application of International Application No. PCT/US2010/037257, filed June 3, 2010; which claims the benefit of U.S. provisional application Serial No. 61/183,775, filed June 3, 2009, all of which are incorporated herein by reference in their entirety.--.

Column 1,
Line 24, "and Gran," should read --and Gratt--.

Column 4,
Line 34, "LU nitrite" should read --to nitrite--.

Column 4,
Line 35, "moleeule" should read --molecule--.

Column 5,
Line 30, "DAF-EM)," should read --DAF-FM),--.

Column 5,
Line 62, "nitrite nitrate)" should read --nitrite + nitrate)--.

Signed and Sealed this
Fifteenth Day of September, 2015

Michelle K. Lee
*Director of the United States Patent and Trademark Office*